US00PP17127P2

(12) United States Plant Patent
Gitzels

(10) Patent No.: US PP17,127 P2
(45) Date of Patent: Oct. 3, 2006

(54) ***DAHLIA* PLANT NAMED 'DAPAPU'**

(50) Latin Name: *Dahlia variabilis*
Varietal Denomination: Dapapu

(75) Inventor: Jeroen Gitzels, Zwaag (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/168,196

(22) Filed: Jun. 28, 2005

(51) Int. Cl.
*A01H 5/00* (2006.01)

(52) U.S. Cl. ..... Plt./321
(58) Field of Classification Search ..... Plt./321
See application file for complete search history.

*Primary Examiner*—Kent Bell
(74) *Attorney, Agent, or Firm*—Wood, Phillips, Katz, Clark & Mortimer

(57) ABSTRACT

A new and distinct *Dahlia* plant named 'Dapapu', characterized by its greyed purple-colored ray florets, yellow-colored disc florets, dark green-colored foliage, and compact, upright, and mounded growth habit.

2 Drawing Sheets

Latin name of genus and species of plant claimed: *Dahlia variabilis*.
Variety denomination: 'Dapapu'.

BACKGROUND OF THE INVENTION

The present invention relates to a new and distinct *Dahlia* plant botanically known as *Dahlia variabilis* and hereinafter referred to by the cultivar name 'Dapapu'.

The new cultivar originated in a controlled breeding program in Rijsenhout, The Netherlands. The objective of the breeding program was the development of freely flowering *Dahlia* cultivars with large flowers and a compact, upright growth habit.

The new cultivar is a naturally occurring whole plant mutation of the commercially available cultivar Dapavio, U.S. Plant Pat. No. 11,492, characterized by its red purple-colored ray florets, yellow-colored disc florets, dark green-colored foliage, and compact growth habit. The new cultivar was discovered as a single plant growing among plants of 'Dapavio' and selected by the inventor on Jan. 1, 2001 at Rijsenhout, The Netherlands.

Asexual reproduction of the new cultivar by terminal stem cuttings since January 2001 at Rijsenhout, The Netherlands and West Chicago, Ill. has demonstrated that the new cultivar reproduces true to type with all characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment such as temperature, light intensity, and day length without, however, any variance in genotype.

The following characteristics of the new cultivar have been repeatedly observed and can be used to distinguish 'Dapapu' as a new and distinct cultivar of *Dahlia* plant:

1. Semi-double greyed purple-colored ray florets and yellow-colored disc florets.
2. Dark green-colored foliage.
3. Compact, upright, and mounded growth habit.

Plants of the new cultivar have larger flowers of a darker color and have a more compact growth habit than plants of the female parent.

Of the many *Dahlia* cultivars known to the inventor, the most similar to the new cultivar is 'Baldelrasp', U.S. Plant Pat. No. 16,167. However, in side by side comparisons, plants of the new cultivar differ from plants of 'Baldelrasp' in the following characteristics:

1. Plants of the new cultivar are more compact than plants of 'Baldelrasp'.
2. Plants of the new cultivar exhibit smaller inflorescences than do plants of 'Baldelrasp'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of the new cultivar. The plants were grown for 11 weeks in a greenhouse at West Chicago, Ill.

Figure 1:
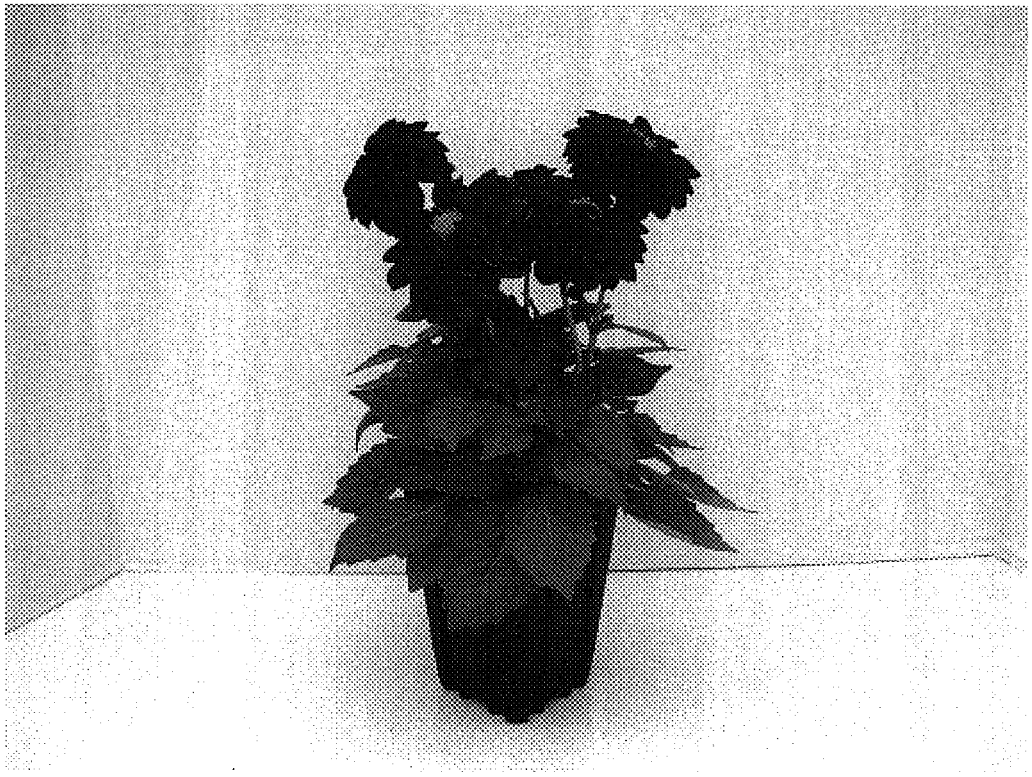
FIG. 1 illustrates a side view of the overall growth and flowering habit of 'Dapapu'.
Figure 2:
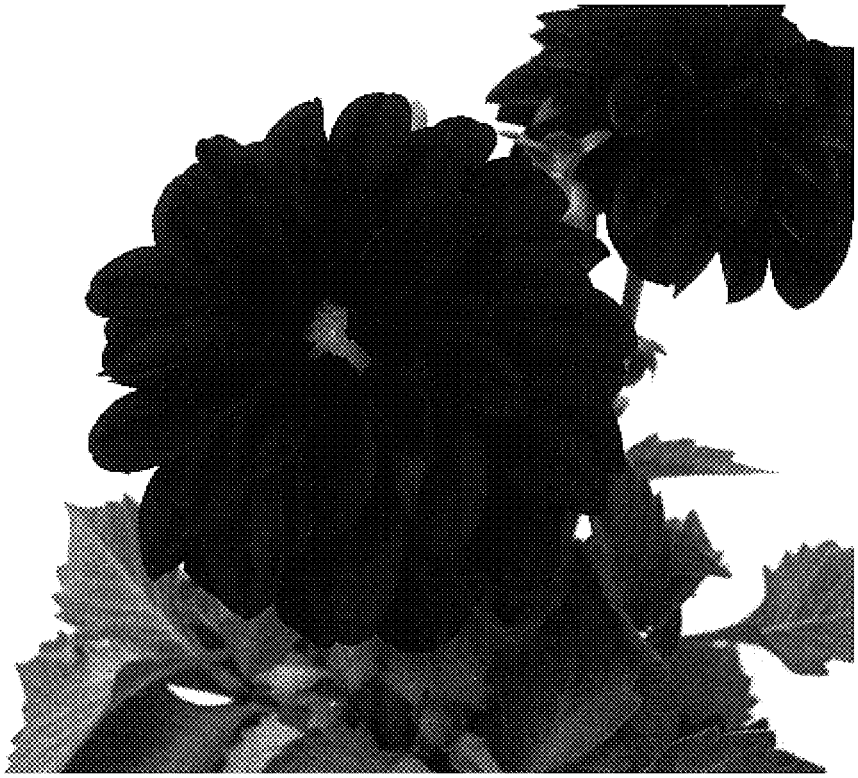
FIG. 2 illustrates a close-up view of a single inflorescence of 'Dapapu' with fully open ray florets and unopen disc florets.
Figure 3:
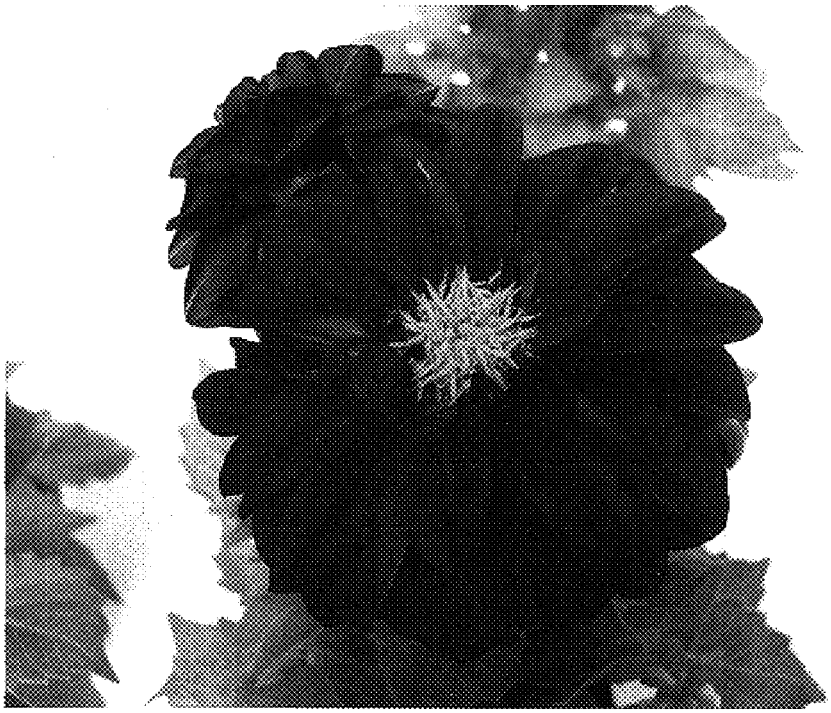
FIG. 3 illustrates a close-up view of a single inflorescence of 'Dapapu' with fully open ray florets and fully open disc florets.
Figure 4:
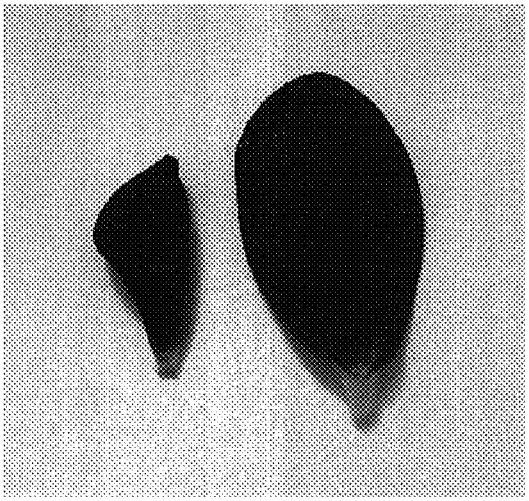
FIG. 4 illustrates a close-up view of the upper surface of the ray florets of 'Dapapu' with a young ray floret on the left and the fully mature ray floret on the right.
Figure 5:
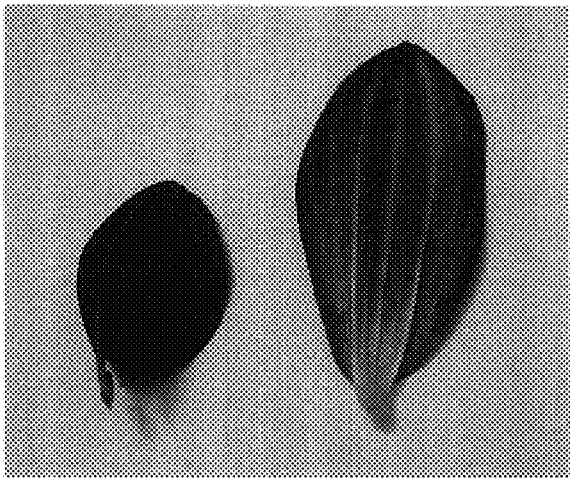
FIG. 5 illustrates a close-up view of the lower surface of the ray florets of 'Dapapu' with a young ray floret on the left and the fully mature ray floret on the right.

FIGS. 4 and 5 further illustrate the variations in color of the ray florets of 'Dapapu'.

DETAILED BOTANICAL DESCRIPTION

The chart used in the identification of colors described herein is The R.H.S. Colour Chart of The Royal Horticultural Society, London, England, 2001 edition, except where general color terms of ordinary significance are used. The color values were determined on Jun. 15, 2005 between 10:00 a.m. and 11:45 a.m. under natural light conditions in West Chicago, Ill.

The following descriptions and measurements describe plants produced from cuttings of stock plants and grown in a double polycarbonate-covered greenhouse under conditions comparable to those used in commercial practice. The plants were grown in 10 cm pots for 11 weeks while utilizing a soil-less growth medium. Greenhouse temperatures were maintained at approximately 65°–75° F. (18°–24° C.) during the day and approximately 60°–65° F. (15°–18° C.) during the night. Greenhouse light levels were maintained at approximately 4,000–6,000 footcandles during the day. Plants were pinched three weeks after planting of rooted cuttings.

Botanical classification: *Dahlia variabilis* cultivar Dapapu.
Parentage: Naturally occurring sport of 'Dapavio'.
Propagation:
- *Type cutting.*—Terminal tip.
- *Time to initiate roots.*—Approximately 7 to 10 days.
- *Time to produce a rooted cutting.*—Approximately 21 to 28 days.
- *Rooting habit.*—Freely branching.
- *Root description.*—Fine, fibrous.
- *Tubers.*—Will form under short day conditions of at least 13 to 14 hours of darkness.

Plant description:
- *Crop time.*—Approximately 6–8 weeks.
- *Growth habit.*—Basal branching, pinching enhances branching.
- *General appearance and form.*—Upright, mounded.
- *Size.*—Height from top of soil to top of plant plane: Approximately 21.2 cm. Height from top of soil to top of foliage: Approximately 14.8 cm. Width/area of spread: Approximately 25.4 cm.
- *Branch description.*—Quantity per plant: Approximately 4. Strength: Strong. Length: Approximately 7.1 cm. Diameter: Approximately 6.7 mm. Length of center internode: Approximately 1.1 cm. Texture: Glabrous. Color: 144A.
- *Foliage.*—Quantity of leaves per lateral branch: Approximately 9. Type: Simple and compound. Quantity of leaflets per compound leaf: 3. Fragrance: None. Arrangement: Opposite. Aspect: At acute angle to stem at first, becoming down-turning with age. Leaf/leaflet: Shape: Ovate. Apex: Acuminate. Base: Obtuse. Margin: Dentate. Venation pattern: Pinnate. Color of upper surface of all leaves/leaflets: Darker than 137A with venation of 143C. Color of lower surface of all leaves/leaflets: N138C with venation of 143C. Texture of upper and lower surface of all leaves/leaflets: Sparse, with more dense pubescence along veins. Length of simple leaf: Approximately 7.9 cm. Width of simple leaf: Approximately 4.9 cm. Length of petiole of simple leaf: Approximately 3.2 cm. Diameter of petiole of simple leaf: Approximately 3.0 mm. Texture of petiole of simple leaf: Glabrous. Color of petiole of simple leaf: 144C with streaks of 59C at base. Length of mature trifoliate leaf: Approximately 8.0 cm. Width of mature trifoliate leaf: Approximately 9.5 cm. Length of petiole of mature trifoliate leaf: Approximately 3.5 cm. Diameter of petiole of mature trifoliate leaf: Approximately 3.7 mm. Texture of petiole of mature trifoliate leaf: Glabrous. Color of petiole of mature trifoliate leaf: 144C with streaks of 59C at base. Length of terminal leaflet: Approximately 6.5 cm. Width of terminal leaflet: Approximately 4.1 cm. Length of petiole of terminal leaflet: Approximately 1.3 cm. Diameter of petiole of terminal leaflet: Approximately 2.4 mm. Length of lateral leaflet: Approximately 5.3 cm. Width of lateral leaflet: Approximately 2.9 cm. Petiole of lateral leaflet: Absent.

Flowering description:
- *Outdoor flowering habit.*—'Dapapu' is freely flowering under outdoor growing conditions with substantially continuous blooming from spring through autumn and year round in greenhouse environment.
- *Time to first flower.*—Approximately 8 weeks.

Inflorescence description:
- *Appearance.*—Type: Composite. Arrangement: Terminal, Arising from leaf axils on strong peduncles, positioned over the foliage. Disc and ray florets arranged acropetally on a capitulum. Persistent.
- *Quantity per plant.*—Approximately 4 fully open at any one time.
- *Lastingness of bloom.*—Approximately 7–10 days.
- *Shape/size.*—Hemispherical. Diameter: Approximately 7.9 cm. Depth: Approximately 4.5 cm. Disc diameter: Approximately 1.5 cm. Receptical diameter: Approximately 9.3 mm. Receptical height/depth: Approximately 2.2 mm. Receptical color: Closest to 150B.
- *Flower bud.*—Quantity per plant: Approximately 2 showing color at any one time. Rate of opening: Generally takes approximately 2 weeks for buds to progress from first color to fully open flower. Shape: Oblate. Diameter/width at first color: Approximately 1.8 cm. Height/depth at first color: Approximately 1.6 cm. Texture: Glabrous. Color: 84D.
- *Fragrance.*—None.
- *Ray florets.*—Quantity: Approximately 60 per inflorescence. Arrangement: Imbricate, in several whorls. Shape: Elliptic, cupped. Apex: Emarginate with three tips. Base: Attenuate, fused to form tube. Margin: Entire. Length: Approximately 2.9 cm. Width: Approximately 1.5 cm. Texture of upper surface: Glabrous. Texture of lower surface: Puberulent. Color of upper surface when just opening: Slightly darker than 187C. Color of lower surface when just opening: Slightly darker than 187C. Color of upper surface when fully opened: 187C with 72A at margin. Color of lower surface when fully open: 72A with ridges of 76C.

Disc florets.—Quantity: Approximately 37. Arrangement: Massed in center of inflorescence. Shape: Cylindrical. Apex: 5 acute tips. Length: Approximately 1.2 cm. Diameter at apex: Approximately 2.2 mm. Diameter at base: Approximately 1.6 mm. Texture: Glabrous. Color: Transparent, closest to 9B.
- *Peduncle.*—Strength: Strong. Aspect: Erect. Length: Approximately 8.5 cm. Diameter: Approximately 2.7 mm. Texture: Glabrous. Color: 144A with streaks of N79A at base.
- *Phyllaries.*—Quantity: One per floret. Shape: Linear, slightly overtapping. Apex: Emarginate. Base: Truncate. Margin: Entire. Length: Approximately 1.6 cm. Width: Approximately 5.8 mm. Texture of upper and lower surfaces: Glabrous. Color of upper and lower surfaces: 150C with 143A at base.

*Secondary phyllaries.*—Quantity: Approximately 5. Shape: Rhomboidal. Apex: Acuminate. Base: Attenuate. Margin: Entire. Length: Approximately 1.1 cm. Width: Approximately 5.1 mm. Texture of upper and lower surfaces: Glabrous. Color of upper and lower surfaces: 137B.

*Reproductive organs.*—Androecium — On disc florets. Stamen number: 5. Anther shape: Linear. Anther length: Approximately 4 mm. Anther color: 7B. Pollen amount: Abundant. Pollen color: 14B. Gynoecium — On disc and ray florets. Pistil length: Approximately 1.2 cm. Stigma length: 4 mm. Stigma color: 17B. Style length: 6.0 mm. Style color: 1C. Ovary length: 2.0 mm. Ovary color: 150C.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Dapapu', substantially as herein shown and described.

* * * * *